(12) United States Patent  
Garcia Da Fonseca et al.

(10) Patent No.: US 8,865,005 B2  
(45) Date of Patent: Oct. 21, 2014

(54) JET DEFLECTION DEVICE

(75) Inventors: Joäo Garcia Da Fonseca, Azambuja (PT); Nuno Alexandre Reis Esteves, Sintra (PT); Robert Burger, Schuttertal (DE)

(73) Assignee: Biosurfit, S.A., Aveiro (PT)

( * ) Notice: Subject to any disclaimer, the term of this patent is extended or adjusted under 35 U.S.C. 154(b) by 757 days.

(21) Appl. No.: 13/125,777

(22) PCT Filed: Oct. 20, 2009

(86) PCT No.: PCT/PT2009/000055  
§ 371 (c)(1),  
(2), (4) Date: Aug. 12, 2011

(87) PCT Pub. No.: WO2010/047609  
PCT Pub. Date: Apr. 29, 2010

(65) Prior Publication Data  
US 2011/0290718 A1    Dec. 1, 2011

(30) Foreign Application Priority Data  
Oct. 23, 2008   (GB) .................................. 0819508.3

(51) Int. Cl.  
G05D 7/06 (2006.01)  
G01N 33/49 (2006.01)  
B01L 3/00 (2006.01)  
B01D 21/26 (2006.01)  
B01D 17/038 (2006.01)  
B01D 17/02 (2006.01)

(52) U.S. Cl.  
CPC ............ *G05D 7/0694* (2013.01); *G01N 33/491* (2013.01); *B01L 3/00* (2013.01); *B01D 17/0217* (2013.01); *B01D 21/262* (2013.01)

USPC ................... 210/787; 210/360.1; 210/380.1; 210/416.1; 494/2; 494/43; 436/45; 436/180; 422/72; 422/505; 422/506; 422/533; 137/1; 137/561 R (58) Field of Classification Search  
CPC ...... G05D 7/0694; G01N 33/491; B01L 3/00; B01D 17/0217; B01D 21/26  
USPC ............ 210/787, 360, 1, 380.1, 416.1; 494/2, 494/43; 436/45, 180; 422/72, 505, 506, 422/533; 137/1, 561 R  
See application file for complete search history.

(56) References Cited

U.S. PATENT DOCUMENTS

| 5,087,532 A | 2/1992 | Challener, IV |
| 5,414,678 A | 5/1995 | Challener, IV |

(Continued)

FOREIGN PATENT DOCUMENTS

| DE | 102005048233 | 4/2007 |
| EP | 0608006 | 7/1994 |

(Continued)

OTHER PUBLICATIONS

International Report on Patentability for PCT/PT2009/000055, issued on Apr. 26, 2011.*

(Continued)

*Primary Examiner* — David A Reifsnyder  
(74) *Attorney, Agent, or Firm* — Patterson Thuente Pedersen, P.A.

(57) ABSTRACT

Devices for controlling fluid flow, in particular microfluidic devices, are described, which exploit gas/liquid interfaces to control liquid flow in accordance with application requirements. Devices for on/off flow switching, centrifugal separation, mixing, metering and aliquoting are described.

35 Claims, 9 Drawing Sheets

(56) References Cited

U.S. PATENT DOCUMENTS

| | | | |
|---|---|---|---|
| 5,508,982 | A | 4/1996 | Challener, IV |
| 5,620,792 | A | 4/1997 | Challener, IV |
| 5,639,567 | A | 6/1997 | Challener, IV |
| 5,751,482 | A | 5/1998 | Challener, IV |
| 5,925,878 | A | 7/1999 | Challener |
| 5,955,378 | A | 9/1999 | Challener |
| 5,986,762 | A | 11/1999 | Challener |
| 5,986,997 | A | 11/1999 | Challener, IV |
| 5,994,150 | A | 11/1999 | Challener et al. |
| 6,063,589 | A | 5/2000 | Kellogg et al. |
| 6,100,991 | A | 8/2000 | Challener |
| 6,230,991 | B1 | 5/2001 | Steinruck et al. |
| 6,235,531 | B1 | 5/2001 | Kopf-Sill et al. |
| 6,277,653 | B1 | 8/2001 | Challener et al. |
| 6,320,991 | B1 | 11/2001 | Challener et al. |
| RE37,473 | E | 12/2001 | Challener |
| 6,344,490 | B1 | 2/2002 | Degeorge et al. |
| 6,625,336 | B2 | 9/2003 | Challener et al. |
| 6,653,152 | B2 | 11/2003 | Challener |
| 6,944,101 | B2 | 9/2005 | Johns et al. |
| 6,944,112 | B2 | 9/2005 | Challener |
| 7,027,700 | B2 | 4/2006 | Challener |
| 7,106,935 | B2 | 9/2006 | Challener |
| 7,266,268 | B2 | 9/2007 | Challener et al. |
| 7,272,102 | B2 | 9/2007 | Challener |
| 7,275,858 | B2 | 10/2007 | Andersson et al. |
| 7,330,404 | B2 | 2/2008 | Peng et al. |
| 7,412,143 | B2 | 8/2008 | Rottmayer et al. |
| 7,440,660 | B1 | 10/2008 | Jin et al. |
| 7,480,214 | B2 | 1/2009 | Challener et al. |
| 7,515,372 | B2 | 4/2009 | Erden et al. |
| 7,580,602 | B2 | 8/2009 | Itagi et al. |
| 7,768,657 | B2 | 8/2010 | Jin et al. |
| 7,796,487 | B2 | 9/2010 | Chu et al. |
| 7,804,656 | B2 | 9/2010 | Gomez et al. |
| 7,830,775 | B2 | 11/2010 | Karns et al. |
| 7,869,162 | B2 | 1/2011 | Lu et al. |
| 7,869,309 | B2 | 1/2011 | Mihalcea et al. |
| 7,893,497 | B2 | 2/2011 | Takasu |
| 8,440,147 | B2 * | 5/2013 | Garcia Da Fonseca et al. ............. 422/503 |
| 2001/0031503 | A1 | 10/2001 | Challener et al. |
| 2003/0128633 | A1 | 7/2003 | Batra et al. |
| 2003/0137772 | A1 | 7/2003 | Challener |
| 2004/0240327 | A1 | 12/2004 | Sendur et al. |
| 2005/0157597 | A1 | 7/2005 | Sendur et al. |
| 2005/0217741 | A1 | 10/2005 | Bohm |
| 2006/0233061 | A1 | 10/2006 | Rausch et al. |
| 2007/0115787 | A1 | 5/2007 | Itagi et al. |
| 2008/0170319 | A1 | 7/2008 | Seigler et al. |
| 2009/0207519 | A1 | 8/2009 | Erden et al. |
| 2009/0208171 | A1 | 8/2009 | Gage et al. |
| 2009/0246082 | A1 | 10/2009 | Saiki et al. |
| 2010/0097901 | A1 | 4/2010 | Challener et al. |
| 2010/0123965 | A1 | 5/2010 | Lee et al. |
| 2011/0044147 | A1 | 2/2011 | Karns et al. |
| 2012/0021447 | A1 | 1/2012 | Da Fonseca et al. |
| 2013/0027688 | A1 * | 1/2013 | Garcia Da Fonseca et al. ............. 356/73 |
| 2013/0074962 | A1 * | 3/2013 | Garcia Da Fonseca et al. ............. 137/597 |
| 2014/0109972 | A1 * | 4/2014 | Garcia Da Fonseca et al. .. 137/1 |

FOREIGN PATENT DOCUMENTS

| | | |
|---|---|---|
| EP | 1 900 433 A3 | 3/2008 |
| EP | 2080554 | 7/2009 |
| JP | 02-280084 | 11/1990 |
| JP | 2004117048 | 4/2004 |
| WO | WO95/33986 | 12/1995 |
| WO | WO97/21090 | 6/1997 |
| WO | WO0146465 | 6/2001 |
| WO | WO03/058641 | 7/2003 |
| WO | WO03060882 | 7/2003 |
| WO | WO03102559 | 12/2003 |
| WO | WO2004003891 | 1/2004 |
| WO | WO2004032118 | 4/2004 |
| WO | WO2004107323 | 12/2004 |
| WO | WO2004003932 | 2/2005 |
| WO | WO2005045815 | 5/2005 |
| WO | WO2007/024829 A2 | 3/2007 |
| WO | WO2007/091097 A1 | 8/2007 |
| WO | WO2008057000 | 5/2008 |
| WO | WO2008060172 | 5/2008 |
| WO | WO2008/080049 | 7/2008 |
| WO | WO2008106782 | 9/2008 |
| WO | WO2010047609 | 4/2010 |
| WO | WO2010077159 | 7/2010 |
| WO | WO2010059736 | 9/2010 |

OTHER PUBLICATIONS

International Search Report for International Application No. PCT/PT2011/000009 dated Oct. 18, 2011.

Grumann et al., "Batch-Mode Mixing on Certrifugal Microfluidic Platforms", Lab Chip. 2005. pp. 560-565.

Haeberle et al., "Certrifugal Micromixer", Chem. Eng. Technology. 2005. pp. 613-616.

Sudarsan et al., "Multivortex Micromixing", Artie McFerrin Department of Chemical Engineering. May 9, 2006. vol. 103, No. 19. pp. 7228-7233.

Nguyen et al., "Micromixers—A Review", Institute of Physics Publishing. Journal of Micromechanics and Microengineering. 2005. pp. R1-R-16.

GB Combined Search and Examination Report for Application no. GB0823660.6 dated May 18, 2009.

GB Response to Search Report for Application No. GB0823660.6 dated Dec. 13, 2010.

International Search Report and Written Opinion for International Application No. PCT/PT2009/000081 dated May 10, 2010.

Fontana, "Theoretical and Experimental Study of the surface plasmon resonance effect on a recordable compact disk", Applied Optics. vol. 43, No. 7B pp. 79-87 Jan. 1, 2004.

Chiu et al., Calculation of Surface Plasmon Effect on Optical Discs, Jap. J. Appl. Phys, Part 1, vol. 43, No. 7B, pp. 4730-4735 (2004).

Notification of Reasons for Refusal for Japanese Application No. 2011-543549, dispatch date May 7, 2013.

Schomburg, W.K., et al., "Microfluid components in Liga technique," *J. Micromech. Microeng.*, vol. 4, pp. 186-191 (1994).

Ducrée, Jens, et al., "The centrifugal microfluidic Bio-Disk platform," *J. Micromech. Microeng.*, vol. 17, pp. S103-S115 (2007).

Furlan, Rogério, et al., "Behavior of microfluidic amplifiers," *Sensors and Actuators*, vol. 51, pp. 239-246 (1996).

Furlan, Rogério, et al., "Comparison of Wall Attachment and Jet Deflection Microfluidic Amplifiers," *Micro Electro Mechanical Systems, 1996, MEMS '96, Proceedings, an Investigation of Micro Structures, Sensors, Actuators, Machines and Systems, IEEE, The Ninth Annual International Workshop on San Diego, CA,* XP010159417, pp. 372-377 (Feb. 11, 1996).

\* cited by examiner

JET DEFLECTION DEVICE

RELATED APPLICATIONS

The present application is a National Phase entry of PCT Application No. PCT/PT2009/000055, filed Oct. 20, 2009, which claims priority from Great Britain Application Number 0819508.3, filed Oct. 23, 2008, the disclosures of which are hereby incorporated by reference herein in their entirety.

FIELD OF THE INVENTION

The present invention relates to devices for fluid handling and methods of using the same for a variety of fluid manipulation operations.

BACKGROUND

Fluid handling is an aspect of analytical procedures involving fluids and in particular to those where minute quantities of chemical or biological substances present in the fluid are to be manipulated or determined. Partially driven by the miniaturization trend observed in the semiconductor industry, a wealth of novel miniaturized microsystems have been developed for analytical purposes giving rise to what is now commonly referred to micro total analysis systems (μTAS) or Lab-on-a-Chip technology. This trend has prompted hydrodynamics with novel challenges for automated fluid handling procedures with sub-milliliter volumes, boosting the rapid growing field of microfluidics based point-of-care/point-of-use technologies.

Microfluidic devices typically refer to networks of flow passages of variable geometry having at least one characteristic dimension on the sub-millimeter length scale. Fluid propulsion may be achieved in a variety of ways including pressure pumping, acoustics, electrokinetics and centrifugation. These networks are able to perform various laboratory unit operations with liquids such as valving, metering, sample splitting, decanting, mixing and reacting. An important aspect of microfluidic technology is fluid gating, which in many embodiments exploits the increasing dominance of surface forces at small length scales of the flow networks to produce passive valves. Typically this is achieved through abrupt changes in the cross section of the liquid passages or by intentionally introducing localised surface modifications for abrupt changes of the liquid-solid wetting behaviour (or both). A common alternative to passive valving is the use of externally actuated valves which are used to temporarily block fluid passages. These latter, however, require the use of additional materials (e.g. flexible membranes) and control circuits for operating the valves, thus increasing the complexity of the device.

It would be desirable for microfluidic devices to possess an inherent ability to perform all liquid handling functions in an automated and flexible way, whilst reducing the complexity of the fluid propulsion and control mechanisms.

SUMMARY

The present invention is set out in the independent claims. Optional features of embodiments are set out in the dependent claims.

Various embodiments of the present invention take advantage of the gas-liquid coupling which develops during flow. This provides opportunities to manipulate the fluid dynamic behavior without the need for moving parts or independent systems to control liquid flow.

In some embodiments a fluid control system is provided which has means for injecting a liquid into a fluid flow control chamber to form a liquid membrane in the chamber dividing it into compartments on each side of the liquid membrane and means for generating a pressure differential between the compartments to control a deflection of the injected liquid jet. The means for injecting may include means for creating a centrifugal force acting on the liquid. The means for generating the pressure differential may include the means for injecting the liquid. The injected liquid may be injected from a reservoir connected to the chamber by a vent. The pressure differential may be generated by the increasing volume of liquid in the control chamber and/or a decreasing volume of liquid in the reservoir as liquid is injected.

In some embodiments, flow may be stopped by deflecting the injected liquid into the vent to form a liquid plug so that flow stops as venting between the control chamber and (liquid feeding) reservoir is prevented. Flow can then be restarted by changing a force acting on the liquid plug to create an imbalance in the pressures which maintain the liquid plug, so that flow is resumed.

The reservoir can be shaped such as to trap a heavier component or components of the liquid in it and to inject a lighter one or ones into the control chamber. Thus, a liquid can be separated into fractions as flow is stopped as described above and once flow is resumed the separated lighter fractions can be recovered in the control chamber. The control chamber may itself be shaped to trap heavier fraction or fractions of the liquid so that an initial liquid flow until the plug forms does not contaminate the separated fraction later on. For the avoidance of doubt the relative terms "heavier" and "lighter" are understood to be relative to each other. The cut-off or threshold between heavier and lighter components or fractions is determined by the specific design and operative parameters of each embodiment.

Some embodiments may provide means for aliquoting the liquid as it is injected into the control chamber or may provide means for injecting the liquid to form a plurality of membranes in the control chamber.

A device for use with the system of the embodiments described above includes in some embodiments a volume and a port through which liquid can be injected into the volume to partition the volume on either side of the liquid and is configured to convert flow of the liquid into the volume (that is an increasing amount of liquid inside the volume) into a pressure differential between the compartments to deflect the injected liquid.

The device may be rotatable about an axis of rotation to centrifugally drive the injection, for example the device may be provided in the form of a "lab on a disc" substrate, resembling an optical disc which can be inserted into a "reader" similarly to known CD players. The device may again be arranged to allow for the centrifugal separation of components by having appropriately shaped volumes connected to each other such that flow between the volumes can be switched on or off.

In some embodiments, the device may be configured to centrifugally separate fractions of a sample, such as separating plasma from a blood sample. The sample volume can, for example, range from 1 to 20 microliters.

The device may comprise other volumes defining fluidic elements such as a metering device. Volumes of the device may additionally be arranged to provide mixing chambers or aliquoting structures.

Further, some embodiments provide methods for controlling fluid flow by deflecting a liquid jet using pressure differentials. In some embodiments, the pressure differential is created by injecting the liquid itself into the chamber and methods of starting and stopping liquid flow by using deflection of liquid to block a vent and subsequently unblock it are further provided.

BRIEF DESCRIPTION OF THE DRAWINGS

Embodiments of the invention are now described by way of example only and with reference to the accompanying drawings, with like reference numerals referring to like parts, in which.

DETAILED DESCRIPTION

In overview devices and methods for manipulating fluids inside fluidic networks, exploring the dynamic coupling between the liquid and gas phases observed in these systems, are now described. An underlying mechanism is the confinement of gas in compartments sharing a liquid interface which is established during flow. Subsequent pressure changes inside the said compartments lead to the deformation or displacement of the liquid interface in a predictable manner. The described fluidic networks are designed to use this effect for a variety of manipulations of practical relevance to fluid handling.

Figure 1A:
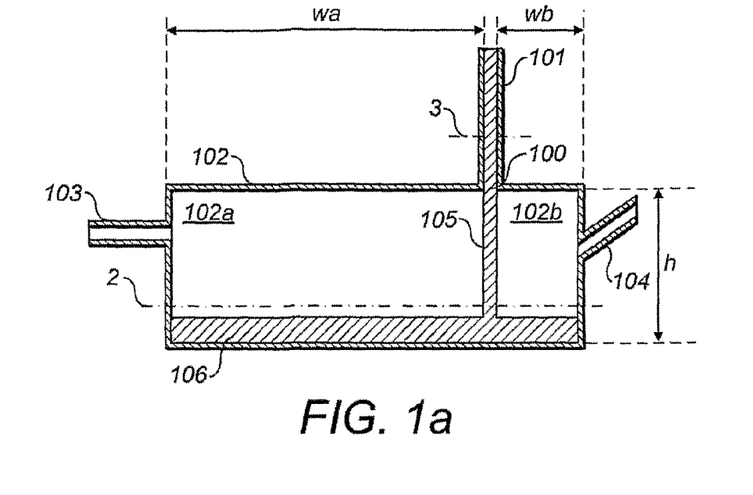
FIGS. 1a, 1b, 1c and 2 illustrate a jet deflection mechanism in a jet deflection device in an embodiment of the invention.
Figures 1B, 1C:
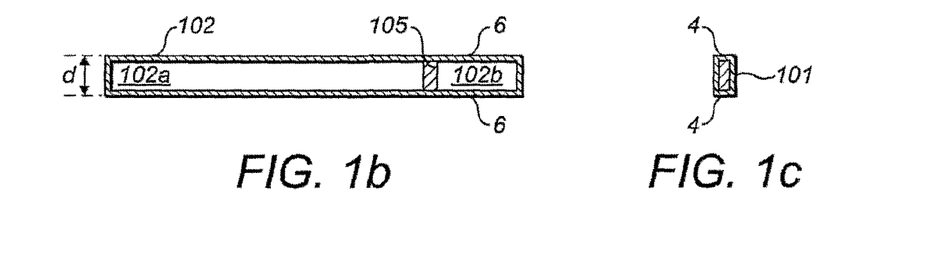

Referring to FIGS. 1a, 1b, and 1c, a principle of operation of a jet deflection device is illustrated in an embodiment of the invention. In FIG. 1a, a liquid jet 105 is issued from the outlet 100 of a passage or channel 101 into the chamber 102. The jet 105 occupies the entire cross section of the chamber 102 as illustrated in FIG. 1b, depicting a cross section along line 2 in FIG. 1a, such that two fluidically separated compartments 102a and 102b are formed, in effect separated by a membrane of liquid. Each compartment 102a and 102b has a separate fluidic port 103 and 104, respectively, associated with it. The corresponding cross-section through the passage 101 (along line 3) is illustrated in FIG. 1c.

The formation of such continuous liquid columns is favoured by the distance between the corresponding respective surfaces 4, 6 confining the liquid in the passage 101 and the chamber 102 in the vicinity of the outlet 100 being of the same order of magnitude. For example, the distances can differ by a factor of up to 5 in some embodiments while they may be substantially the same in others. In some embodiments, these distances are of capillary dimensions, i.e., smaller than 1 mm and, in some embodiments, smaller than 500 micron, as the increasing dominance of surface forces at smaller dimensions provide for enhanced liquid jet integrity. The establishment of the jet requires a continuous flow of liquid and within time, this flow leads to the accumulation of a liquid volume 106 in the chamber 102.

We now consider the case of continuous filling of the chamber 102 by a continuous jet 105 occupying the cross section as illustrated in FIGS. 1b and 1c. For now, we assume that the ports 103 and 104 of the two compartments 102a, b are closed. The fluidically disconnected chambers 102a and 102b have volumes $V_i$ with the index i representing the two compartments a and b, respectively. For the sake of simplicity, we assume a rectangular chamber geometry defined by the height h, the width $w_i$ (with i={a, b} and the depth d (distance between the two surfaces 6). The volumes of the two compartments $V_i = w_i * h * d$ are defined by their respective widths $w_i$. In presence of a density dependent volume force represented by the arrow 150 such as gravity or a centrifugal force, a compact liquid volume will accumulate at the bottom of reservoir 102 with a level initially located at $z_i$ and later at $z_i'$.

As the liquid jet 105 is injected into the chamber 102, the gas volume in both compartments will be compressed due to the increasing space occupied by the liquid volumes.

So the gas pressure at a given point in time is given by:

$$p_i' = p_i \frac{V_i}{V_i'} = p_i \frac{(h-z_i)w_i d}{(h-z_i')w_i d} = p_i \frac{h-z_i}{h-z_i'}$$

The pressures observed in both compartments will continuously rise as $z_i' > z_i$. Note that $p_i'$ is independent of the width of the compartment $w_i$. If we now assume that the two compartments have the same initial pressures, i.e. $p_{102a} = p_{102b} = p_o$ and the same liquid level at all times, i.e. $z_a' = z_b' = z'$ and, for the sake of simplicity assuming $z_a = z_b = z$, we obtain $$p_i' = p_0 \frac{h-z}{h-z'}$$

which is evidently independent of the particular compartment i. This means that in the described situation, no pressure difference $\Delta p = p_{102a} - p_{102b} = 0$ will apply across the liquid jet.

Figure 2:
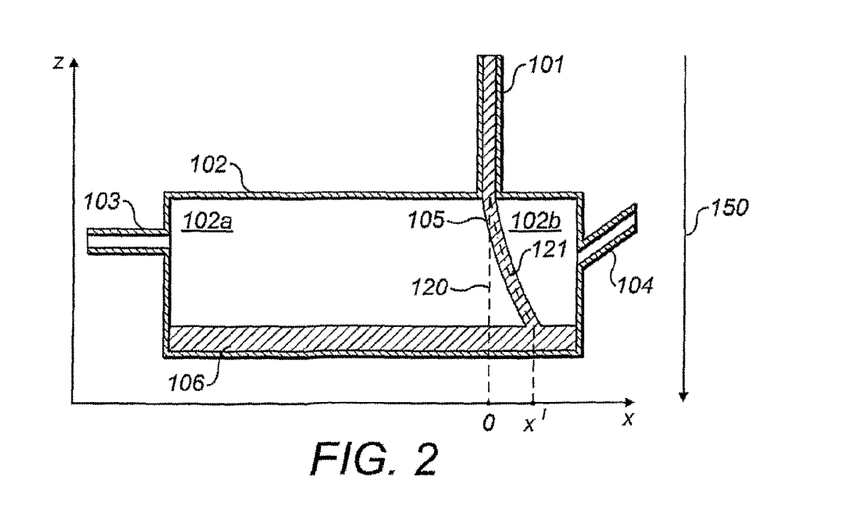

Referring to FIG. 2, we assume that the port 103 of chamber 102a is still closed or connected to a constant pressure $p_{102a}$ while outlet 104 is connected to a pressure $p_{102b}$. Now a finite pressure difference $\Delta p = p_{102a} - p_{102b} \neq 0$ will apply across the jet which is consequently deflected from its pressure balanced straight path 120 towards the lower pressure outlet (104 in FIG. 2) along a curved path 121. The deflection can be measured by the deviation x' of the jet hitting the liquid surface at the bottom of the reservoir 106 with respect to the position of the straight path at x=0.

The pressure difference resulting from liquid flow responsible for the initial deflection of the liquid jet can be controlled by adjustments to the fluid propulsion mechanism and/or incorporating internal elements specifically arranged in the fluidic network to interact with the flowing liquid. In some embodiments, liquid flow induced jet deflection is used in order to close or open gas passages present in the receiving chamber 102 to enable the adjustment of the pressure in the different compartments of the fluidic system or provide for abrupt transitions in gas-liquid fluid dynamics by temporarily or permanently introducing liquid plugs into gas passages. In some embodiments, an additional liquid present in the fluidic network is used in order to close or open additional gas outlets of the fluidic network that enable the adjustment of the pressure in the different compartments which are formed once the liquid jets develops. This internal control may be used in order to obtain a constant or a variable (for example oscillating) pressure difference between at least two compartments 102a, b of the receiving chamber 102.

In some embodiments, a centrifugal force is used both as a fluid propulsion and control mechanism, for example in systems based on a rotating device, such as a disc or a rotor. In these embodiments control of the centrifugal frequency of the substrate containing the fluidic network is sufficient to act as fluid propulsion and control mechanism, reducing the overall system complexity and potentially eliminating the need for external active or passive elements such as pumps, tubes and valves.

The centrifugal force is given by:

$$\vec{f}_\omega = -\rho \vec{\omega} \times (\vec{\omega} \times \vec{r})$$

depending on the density ρ, the radial position from the center of rotation r, and the centrifugal frequency ω.

In this case also the Coriolis force $$\vec{f}_C = -2\rho \vec{\omega} \times \vec{v}$$

for the flow velocity v needs to be considered for the deflection of the liquid jet 105. Previous work has shown that the Coriolis force becomes increasingly important at high centrifugal frequencies, and that it can be used to route liquids to specific paths by controlling the rotation frequency. For example it is possible to selectively direct liquids into either branch of a bifurcation by reversing the sense of rotation. However, experiments in typical configurations of the described embodiments have shown that the Coriolis force is not the dominating force governing the deflection of the liquid jet as the direction of deflection does not reverse when the sense of rotation is reversed. Accordingly, the Coriolis force can be neglected by way of approximation.

Figure 3:
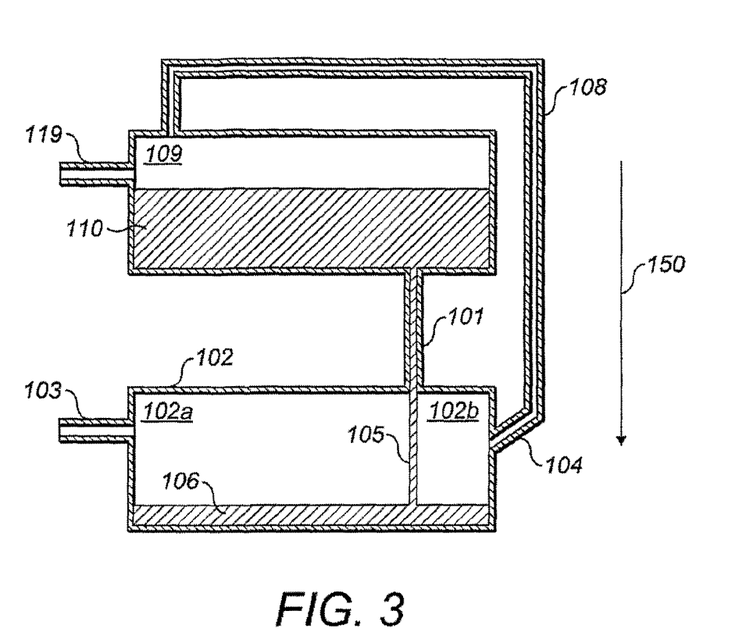
FIGS. 3 and 4 illustrate an arrangement enabling the use of the jet deflection mechanism to introduce a liquid plug into a fluidic connection for providing transitions in the liquid-gas coupling and hence the flow properties in an embodiment of the invention.

Referring to FIG. 3, a specific embodiment of internal control of the pressure difference developing during flow is illustrated in an embodiment of the invention. The port 104 of the compartment 102b is fluidically connected via a channel 108 to an upstream reservoir 109 at the pressure $P_c$ while the port 103 remains closed to atmospheric air. The reservoir 109 contains a liquid volume 110 supplying liquid to channel 101. Assuming that the liquid jet is established and that a port 119 to the reservoir 109 is closed to atmospheric air, there are now three compartments, 102a, 102b and 109, whereby compartments 109 and 102b are fluidically connected by the channel 108 thus $p_{109} = p_{102b}$. With time, the increasing liquid level of the volume 106 and the corresponding decrease in the liquid level of the volume 110 lead to, respectively, an increase of $p_{102a}$ and a decrease of $p_{102b}$ so that $p_{102a} > p_{102b}$. This pressure imbalance tends to displace fluid from the compartment 102b through 104 and 108 into 109, leading to a deflection of the liquid jet 105 in the positive x direction, as described above. If one of the volumes 109 and 102b is connected to atmospheric air or other structures of significantly larger volume, the corresponding pressure will stay substantially constant or change only by a small amount but the volume change of the other, isolated volume would still act to create the pressure imbalance and deflect the jet.

Figure 4:
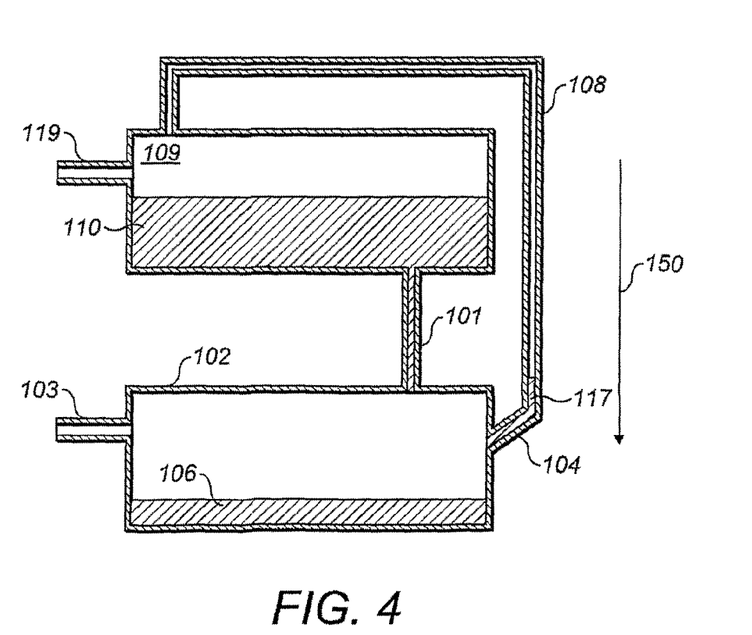

Referring to FIG. 4, a case where the liquid jet itself is deflected into the port 104 is illustrated in an embodiment of the invention. Given appropriate conditions, the liquid column of the jet 105 breaks, leaving a liquid plug 117 blocking the passage of gas from the pressurized compartment 102b to the reservoir 109. As a result, compartment 102a and b are merged and the pressure difference between 102a and 102b will be equilibrated so that $p_{102a} = p_{102b} = p_{102}$ and $p_{102} > p_{109}$. Under certain conditions, a metastable equilibrium can be reached soon after plug 117 is formed and the plug remains essentially stationary inside the channel 108 and no liquid is displaced from the reservoir 109 to the chamber 102. The plug behaviour is determined by the balance between the pressure difference responsible for its introduction in the port 104, the pressure on the liquid plug resulting from the applied fluid propulsion mechanism and the capillary pressure due to the contact of the liquid with the walls of the passage 108.

It is possible to move from this metastable equilibrium condition, by creating an imbalance between these pressures. For example, it is possible to act on the port 119 in order to create a pressure imbalance. For systems using a centrifugal force as fluid propulsion mechanism, this imbalance can easily be achieved by changes of the centrifugal frequency. In both cases the plug will either move through the channel 108 into the reservoir 109 or back into the chamber 102. Once the plug is removed, liquid will again be displaced from the reservoir 109 to the chamber 102. Depending on externally imposed conditions, the geometry and dimensions of the flow network, the system may reach the metastable condition at least once more or displace all the liquid from the reservoir 109 into the chamber 102.

In some embodiments, the configuration described above with reference to FIGS. 3 and 4 is implemented as an ON/OFF flow switch device. In this case, liquid will flow (ON state) to the receiving chamber 102 until the jet is deflected into outlet 104 forming the liquid plug 117. Once the plug has been formed and while it remains stationary inside the passage 108 no liquid is issued from the outlet of channel 101 (OFF state). Because the fluid propulsion mechanism is still being applied, the device can be performing other functions with liquids present in adjacent structures. Flow is resumed either only once or several times by acting upon the fluid propulsion mechanism as described above. This provides opportunities to synchronize simultaneous events occurring in multiple structures of a single fluidic device.

Depending on the specific application, the reservoir 109 is designed to determine whether all of the volume initially present in the reservoir 109 is transferred to chamber 102 or if a certain fraction is retained in the reservoir 109. In embodiments for separating different components present in a liquid based on their different densities, one or more of the separated fractions are retained partially or totally in the reservoir 109 due to the shape of the reservoir. Furthermore, in some embodiments the chamber 102 is designed to retain one or more of the different density fractions in order to ensure that only the desired fraction or fractions proceed to other fluidic structures.

Figure 5A:
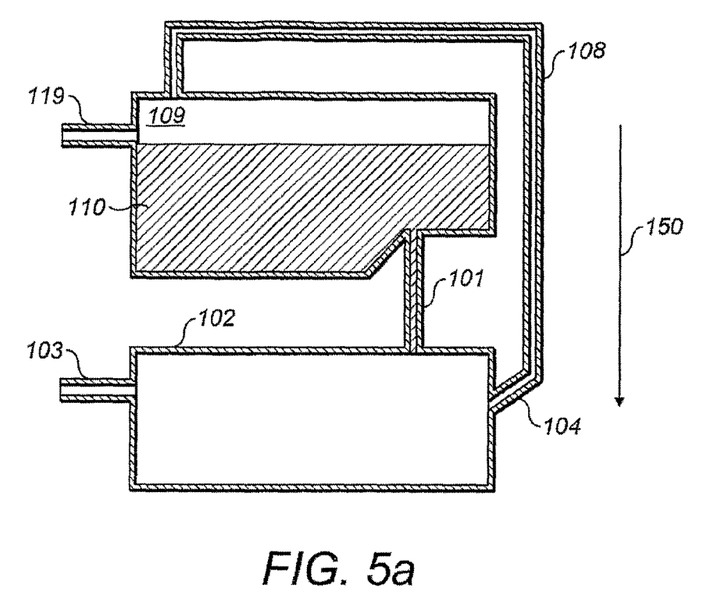
FIGS. 5a to 5e illustrate an example of the jet deflection mechanism of FIGS. 3 and 4 being used for the separation of fluid constituents according to their density in an embodiment of the invention.

Some embodiments provide a two-phase liquid separation device such as, for example, for the separation of the cellular components present in whole blood from plasma. FIG. 5a is a schematic illustration of a possible device configuration. Initially the two-phase liquid is in the reservoir 109. Passages 103 and 119 are either closed to atmospheric air or lead to other structures present in the device which are closed to atmospheric air, such that gas is not able to escape from the fluidic structure. Upon application of a fluid propulsion mechanism, such as a density dependent volume force, for example a centrifugal force, a continuous jet is formed, dividing the chamber 102 into two fluidically separated compartments.

Figure 5B:
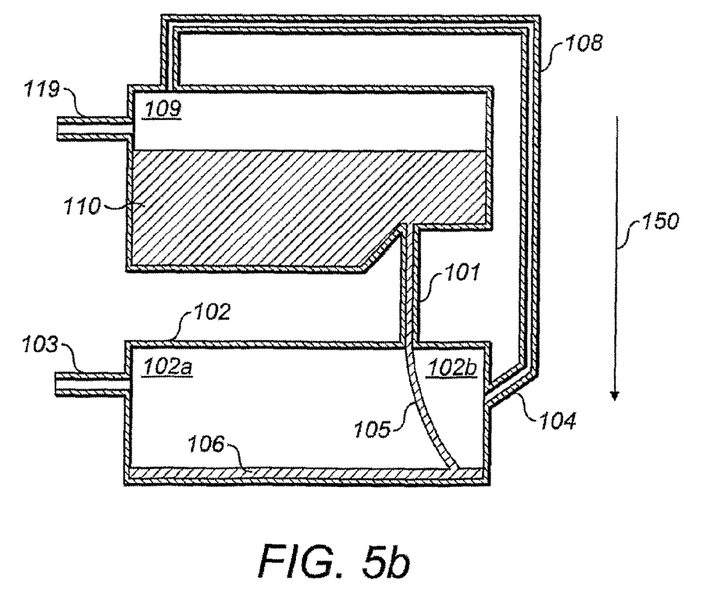
Figure 5C:
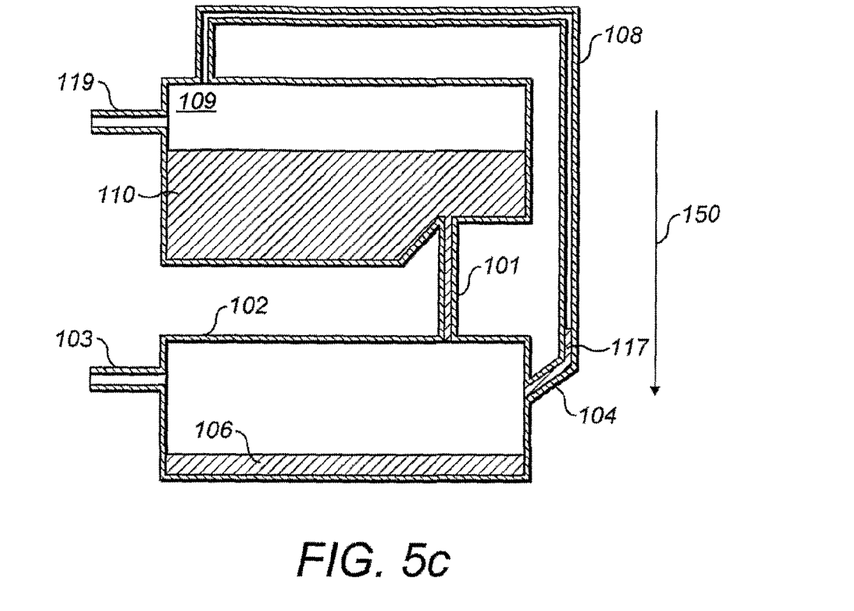

Due to the pressure difference created by the decreasing liquid level in reservoir 109 and/or the increasing liquid level in the chamber 102, the liquid jet 105 is deflected in the chamber 102 towards the outlet 104 as illustrated in FIG. 5b. At a certain moment the jet is forced into outlet 104 and forms the liquid plug 117 in the passage connecting the reservoir 109 to the chamber 102 (FIG. 5c) leading to the metastable equilibrium condition described earlier.

Figure 5D:
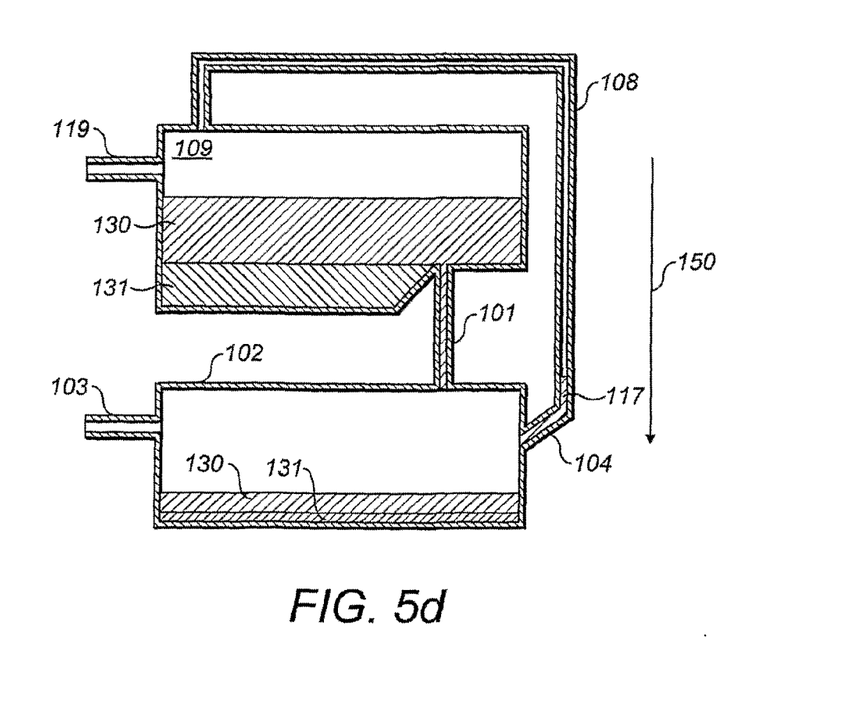
Figure 5E:
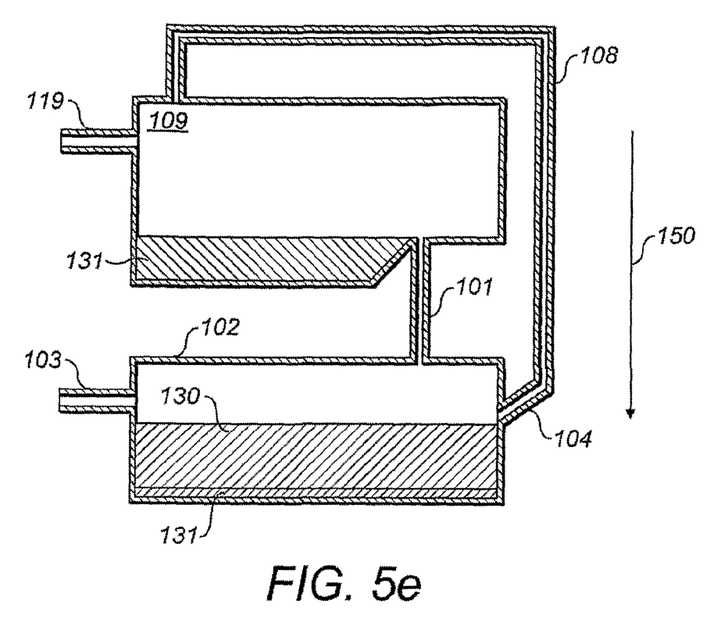

At this point liquid flow stops but the liquid propulsion mechanism is still being applied. As a result, the denser phases present in the liquid sediment according to the direction of the force field, and two different phases or fractions 130 and 131 are obtained both in the reservoir 109 and the chamber 102, as illustrated in FIG. 5d. Upon removal of the liquid plug obstructing the passage between the reservoir 109 and the chamber 102, the flow resumes again and the separated fluid 130 is moved from the reservoir 109 to the chamber 102 (FIG. 5e). The location, geometry and dimensions of the port 103 determines the fraction of liquid in the chamber 102 which proceeds to adjacent fluidic structures. One skilled in the art readily realizes that the passage may be formed in several shapes, and in some embodiments the passage is designed such that only the separated fraction or fractions of liquid 130 proceeds to subsequent structures.

Figure 5F:
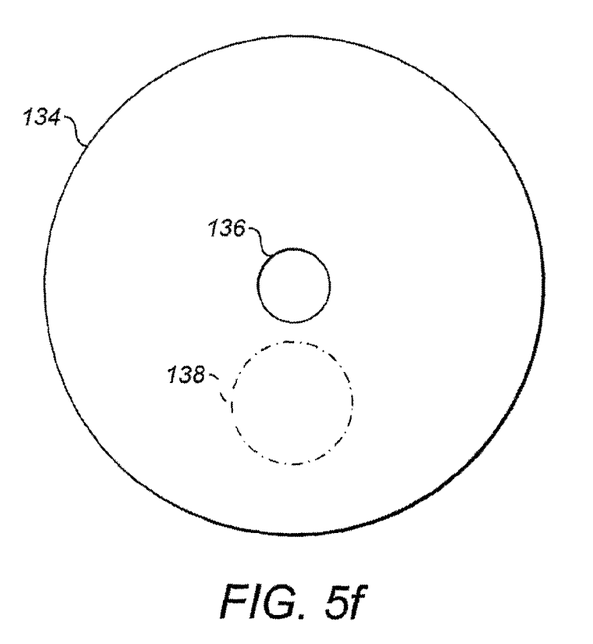
FIGS. 5f to 5h illustrate a centrifugal embodiment of the invention on a rotatable disc.
Figure 5G:
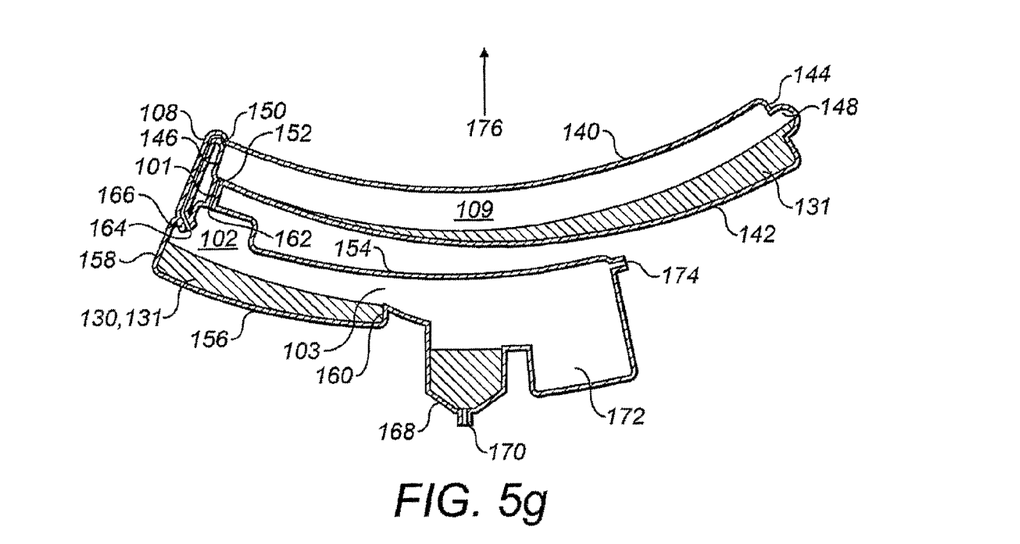
Figure 5H:
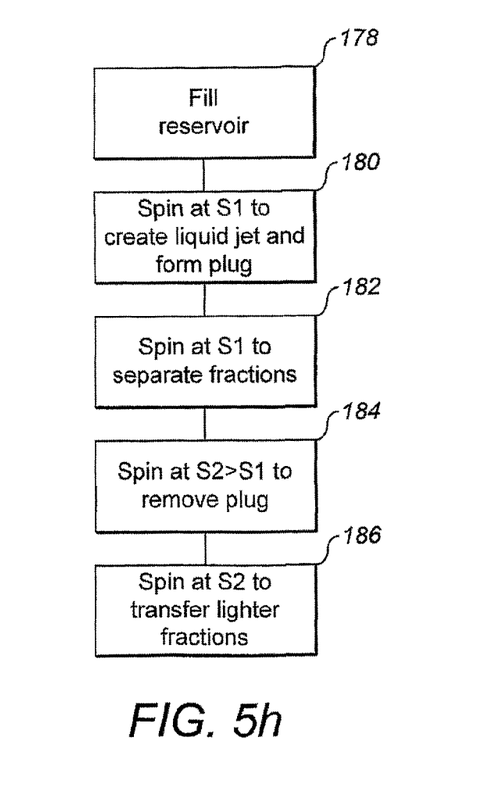

Referring to FIGS. 5f to 5h, a centrifugal embodiment for the separation of mixtures of liquids having different densities or the separation of solid material from suspension, in particular separating blood cells from blood plasma, is now described.

A disc 134 similar to known optical discs such as CDs and known in the art as a "lab on a disc" is manufactured from thermoplastic polymers including various grades of PMMA (polymethyl methacrylate), PC (polycarbonate), PS (polystyrene), COP and COC (cycloc olefin polymers and co-polymers), to give a transparent substrate which is suitable for optical detection methods for detecting the materials separated with the device. The disc 134 is manufactured using injection molding or injection/compression molding although other forming methods such as hot-embossing can equally be employed. These devices need to be assembled in order to provide a fluidic network. This can be achieved using lamination of thin foils or employing adhesive materials such as terminally activated glues, photopolymers, reactive systems or solid adhesives. Further manufacturing alternatives include lithography using commercial photo resist to generate fluidic networks in the disc 134, laser ablation or micromilling.

The disc 134 defines a central aperture 136 which is arranged to engage with a corresponding detent of a rotatable table of a control and reading device, as is well known in the art of centrifugal microfluidics. One or more microfluidic elements as described above are formed in the disc, one of which is schematically indicated by the dashed circle 138.

With reference to FIG. 5g, the microfluidic element 138 comprises a chamber 102 and a fluid reservoir 109 connected to each other by a passage 101 for carrying liquid from the reservoir 109 to the chamber 102 as the disc 134 is spun, and a venting passage 108 connecting the chamber 102 to the reservoir 109 for pressure equilibration. The chamber is defined between opposed surfaces for constraining a liquid jet injected from the passage 101, as described above. The axis of rotation within the aperture 136 is not shown in FIG. 5g but is located off the figure as indicated by arrow 176.

The reservoir 109 is defined by a first reservoir wall 140 radially intermediate an axis of rotation defined by the aperture 136 and a second reservoir wall 142, as well as respective side walls 144 and 146 at either end of the first and second walls 140 and 142. A sample inlet 148, for example a blood inlet, is defined in the side wall 144, connected to further sample delivery structures or arranged to introduce a sample into the reservoir 109 by capillary action. Sealing devices (not shown) are provided to close access from outside the disc to the sample inlet 148 once a sample has been loaded into the microfluidic element 138. This prevents contamination and seals the sample inlet 148 from atmospheric air. In some embodiments, an adhesive flap is used to seal the sample inlet 148.

At or adjacent to a side wall 146 opposed to the side wall 144, a port 152 establishing fluidic communication between the reservoir 109 and the passage 101 is provided in the second reservoir. The second reservoir wall 142 is arranged in relation to the port 152 such that it extends radially beyond the port 152 to define a holding volume for holding a first fraction 131, for example cellular material from a blood sample, and preventing its passage through the port 152. Similarly, a port 150 is defined generally in the first reservoir wall 140, in some embodiments specifically between the side wall 146 and the reservoir wall 140 to provide fluidic communication with the vent passage 108.

Turning now to the chamber 102, the chamber 102 is defined by a first chamber wall 154 radially between a second chamber wall 156 and the reservoir 109, as well as side walls 160 and 158 at opposed ends of the chamber 102. The first chamber wall 154 defines a port 162 providing fluidic communication with the passage 101 and a port 164 is provided to one side of the port 162 in the side wall 158. The port 164 is provided in a projection 166 extending from the side wall 158 so that it is disposed adjacent a liquid jet issuing from port 162, to facilitate plug formation as described above. The projection 166 ensures that the port 164 is closer to the location of an undeflected jet from port 162 (the straight line continuation of passage 101), than it would be if being defined flush with wall 158. The projection, and final portion of passage 108 contained therein are angled obliquely in relation to a radial direction, to facilitate dislodging of any plug formed in the passage 108 by centrifugal forces.

The passage 103 from the chamber 102 to adjacent structures is defined between a termination of the wall 160 and the first wall 154 to define a fraction retaining portion of the chamber 102 extending radially beyond port 103 such that heavier fractions received in the chamber 102 from the reservoir 109, for example blood cells, are retained, while lighter fractions, for example blood plasma, can flow through the port 103 to adjacent structures, for example a metering structure. Such metering structures are well known in the art and, in one embodiment, comprises a metering volume 168 connected by a valve 170 to subsequent structures and an overflow volume 172 for accepting any overflow from the metering volume 168. The valve 170 is a capillary valve, surface coating valve or a siphon in various embodiments.

The adjacent structure further comprises an air vent 174, which connects the metering and overflow volumes 168, 172 and, thus, in use, the compartment 102b, to a circuit open to atmospheric air for pressure equilibration.

In the embodiments described with reference to FIGS. 3 to 5, there are two contributions to the pressure differential across the liquid jet issuing from passage 101. On the one hand, pressure increases in the compartment not connected to the passage 108, assuming that the port 103 is closed to atmospheric air or connected to other structures which are closed to atmospheric pressure and are not significantly bigger than the volume of the chamber 102. On the other hand, the flow of liquid from the reservoir 109 to the chamber 102 creates a negative pressure in the chamber 109, assuming that it is not connected to atmospheric air. This negative pressure is applied via passage 108 to the portion of the chamber on the other side of the jet issuing from the passage 101. Therefore, if both the reservoir 109 and the chamber 102 are not connected to atmospheric pressure, the pressure differential resulting in the deflection of the liquid jet into the passage 108 is due both to a negative pressure on one side of the jet and a positive pressure on the other side of the jet. However, either one of these pressures alone can be employed to achieve the deflection of the liquid jet, if one of either the reservoir 109 or the chamber 102 are connected to atmospheric pressure.

Operation of the centrifugal embodiment described above is now described with reference to FIG. 5*h*. At step 178, the reservoir 109 is filled with a sample and at step 180 the disc 134 is spun at a speed s1 to create a liquid jet issuing into chamber 102 from the passage 101 and to form a plug in the passage 108, as described above. This, in effect, switches the liquid jet off so that most of the sample remains in the reservoir 109. A small amount of the sample is transferred to the chamber 102 before a plug is formed but the dimensions of the chamber 102, the relative locations of the ports 162 and 164 and the speed s1 are selected so as to ensure that the volume of liquid injected into the chamber 102 does not exceed the fraction retaining volume of the chamber 102 so that no liquid is entering the port 103 before the removal of the plug described below.

At step 182 the disc is continued to be spun at speed s1 to centrifuge the sample in order to separate the fractions (for example separating blood cells from plasma) until satisfactory separation is achieved. Then, at step 184, the disc is spun at an increased speed s2 to eject the plug 108 into the chamber 102, thus reopening, in effect, the passage 101 so that the separated lighter fraction (e.g. plasma) is now transferred to the chamber 102 through the passage 101 and then to subsequent chambers through the port 103 as the disc is continued to be spun at speed s2 at step 186. It will be understood that other sequences of spinning speeds are equally possible to achieve the same end, for example including more intermediate speeds. In some embodiments, the speed s2 may be lower than the speed s1 to create an imbalance of pressures which acts to dispel the plug 108 into the reservoir 109 rather than to the chamber 102, depending on the specific application of the device, as well as the positioning of the structure in relation to the centre of rotation.

The embodiment described above in relation to FIGS. 5*f* to *h* is particularly suited to the separation of blood plasma, since the corpuscular components of blood are denser than plasma serum and hence sediment under centrifugation against the walls 142 and 156 forming a cell compact, thus allowing for the extraction of plasma. The microfluidic structure described above with reference to FIG. 5*g* can readily be manufactured with the length scale indicated in the figure, for the separation of plasma from blood samples ranging from 1 to 20 microliters, depending on the depths used for the different features. This range can be easily extended to smaller or larger volumes by design changes to the dimension and geometry of the structure. Typical time scales for the separation process from plug formation to extracting the plasma are within tens of seconds and hence the processes is highly suited to rapid testing schemes such as those required in point of care or point of use devices.

In some embodiments, the liquid jet deflection mechanism is explored for liquid mixing operations. This is particular relevant to microfluidic devices given the laminar flow regimen commonly observed in these systems, which hinders homogeneous mixing. In some embodiments, the reservoir 109 contains a first liquid, and the receiving chamber 102 contains a second liquid. The presence of an additional liquid in chamber 102 does not affect the essence of the above analysis of the jet deflection mechanism. The deflection of the liquid jet 105 increases the contact surface with the liquid present in chamber 102 leading to a faster and more uniform mixing compared to the case where the liquid jet is not deflected. In some embodiments allowing for faster mixing, the switch mechanism previously described is used to intersperse several ON/OFF states to discretely inject the small portions of a first liquid present in the reservoir 109 onto the second liquid present in the chamber 102.

Figure 6:
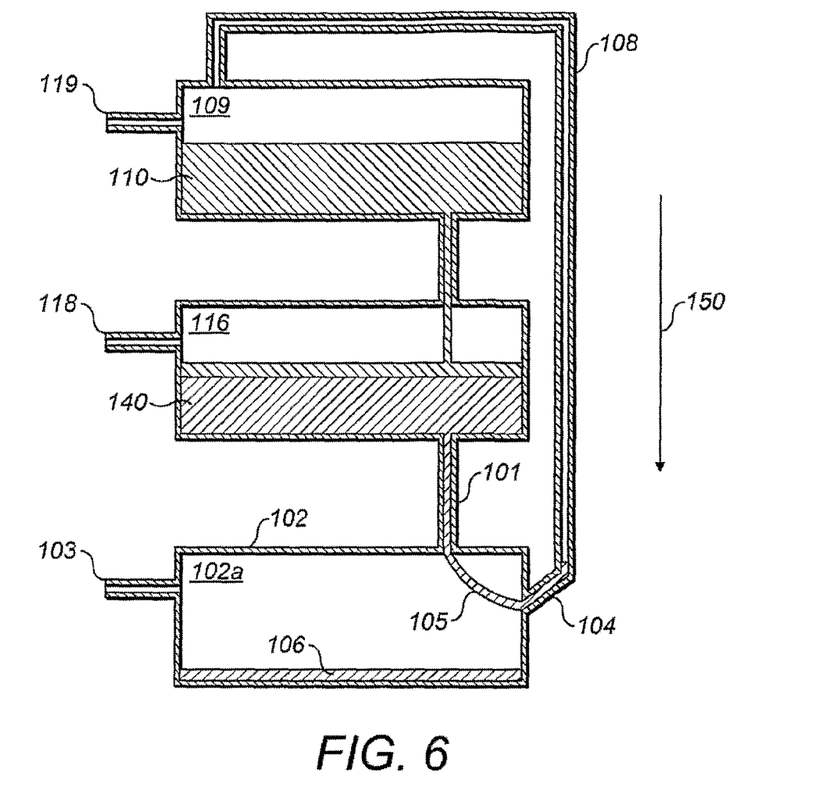
FIG. 6 illustrate a configuration for liquid mixing in an embodiment of the invention.

Referring to FIG. 6, embodiments which use the ON/OFF switch mechanism for liquid mixing, a further chamber 116 is included between the chamber 102 and the reservoir 109, are schematically illustrated. In this case a first liquid present in the reservoir 109 flows into the further chamber 116 and a second liquid flows from the further chamber 116 into the chamber 102. A continuous liquid jet 105 is formed in the receiving chamber 102 and deflects into the port 104 that is used to equilibrate the gas pressure between the reservoir 109 and the chamber 102. The OFF state of the fluidic switch is then activated by introducing a liquid plug into the channel 108, as described above, and the flow to the receiving chamber 102 comes to a halt. The pressure conditions in the reservoir 116 are controlled by acting on the port 118 and determine whether flow from the reservoir 109 to the chamber 116 continues or also comes to a halt. In this second case it suffices that the port 118 is either closed or leads to fluidic structures closed to atmospheric air, and the resulting delay enables further mixing of the fluids in reservoir 116 by diffusion. In some embodiments, the ON state of the fluidic switch is activated by moving the liquid plug from the outlet 104 directly into the reservoir 109. This will further enhance the mixing, as a fraction of the second liquid will mix in the first reservoir 109 initially containing only the first liquid. The device can be operated in such manner that the process described is repeated several times until all liquid has been dispensed to the chamber 102.

Figure 7A:
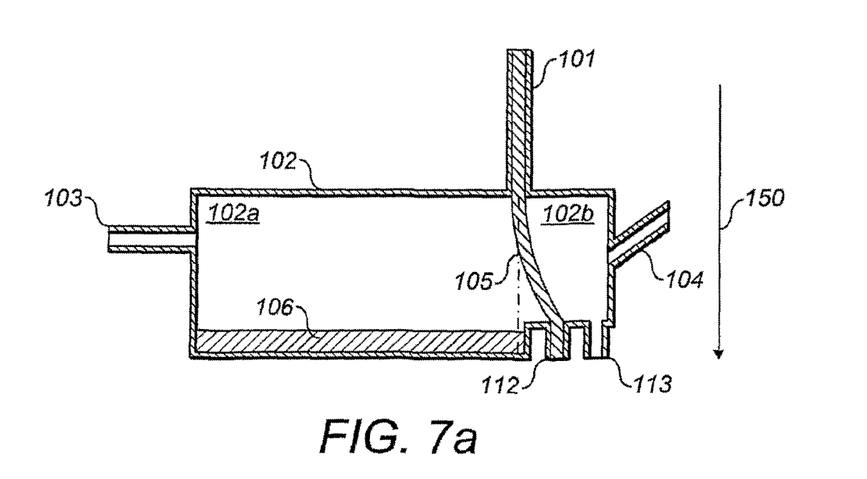
FIGS. 7a and b, illustrate configurations for liquid routing and aliquoting in an embodiment of the invention.

Some embodiments provide devices for liquid routing and liquid splitting into fractions (also referred to as aliquoting). Liquid routing enables selectively directing liquid or fractions thereof into outlets placed in specific locations of the chamber 102. FIG. 7*a* is a schematic illustration of a liquid routing structure using the liquid jet deflection mechanism discussed above. Although not shown in the figures, in some embodiments, the liquid for jet formation is issued from a reservoir like the reservoir 109 described above, with similar or equivalent connections to the chamber 102. The liquid jet 105 is deflected from its initial position, and is thereby directed to specific outlets 112 and 113 that route the liquid, for example a determined volume of liquid, into downstream fluidic elements of the network. The chamber 102 may contain a multitude of elements similar to the outlets 112 and 113 of fixed or variable geometry and dimensions. The volume of liquid which is directed to each outlet can be controlled via the fluidic network design and/or adjustments to the fluid propulsion operating parameters. This provides for the opportunity for routing variable liquid volumes to different locations via changes to the propulsion mechanism for the same fluidic network design. By contrast, in known devices the design of the network is used to determine a fixed amount of liquid which is routed or aliquoted.

Figure 7B:
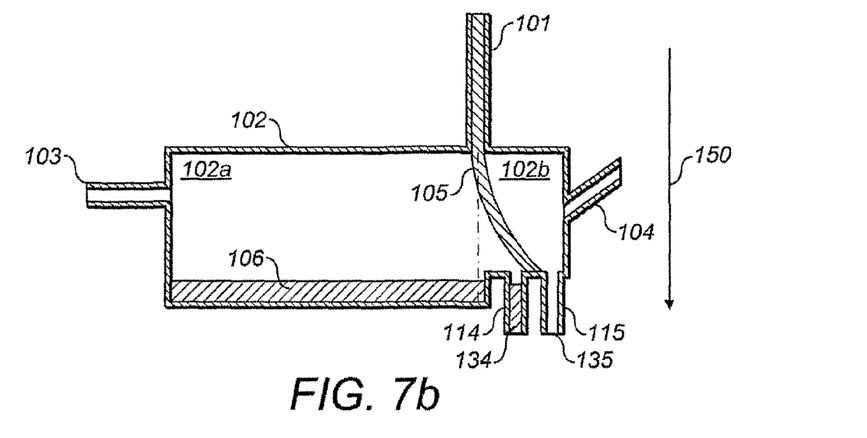

Referring to FIG. 7*b*, an aliquoting structure is depicted in an embodiment of the invention. The liquid jet 105 is deflected from its initial position, and during deflection fills partially or totally the receiving reservoirs 114 and 115 in fluidic communication with the outlets 134 and 135. These outlets connect to downstream fluidic structures and may consist of fluidic elements such as capillary valves, surface modification valves, pressure actuated membrane valves, piezoelectric valves, phase-change valves or siphons. The design and actuation of these are familiar to those skilled in the art. The receiving chamber 102 may contain a multitude of elements similar to receiving reservoirs 114 and 115 of designed volumes for liquid metering. For applications requiring the complete volume of the receiving reservoirs, an additional reservoir used as an overflow for retaining the liquid excess, whilst ensuring adequate filling of all aliquoting reservoirs is added in some embodiments. The aliquoted liquid fractions are passively defined by the geometry and dimensions of the aliquoting elements or by actively controlling the deflection in order to obtain defined volumes in specific locations 114 and 115 without completely filling these reservoir parts.

The device described with reference to FIGS. 7a and b can be operated in a number of ways, depending on whether the ports 103 and 104 are opened or closed. If both ports are closed, the liquid will deflect and leave from the nearest outlet unless the liquid is held by another mechanism, such as the valves described with reference to FIG. 7b, or by entrapping liquid into a downstream gas passage or in case of a centrifugal system incorporating a siphon. In this case, the liquid completely fills that exit and the liquid level inside the chamber 102 will rise again as a result, the liquid membrane deflects to the adjacent outlet, and the process continues. Closing port 103 and leaving port 104 open provides the opportunity to continuously deflect the liquid jet over the top of the outlets, allowing for controlled volumes to be introduced into these. This can be done by externally imposing a negative pressure in outlet 104 or, for example, connecting it to a reservoir like reservoir 109 described above (using the decrease in liquid level in this reservoir and an associated negative pressure to continuously deflect the liquid jet). Leaving port 103 open could enable, for example, extracting liquid from this port at a later stage, using an overflow principle as described above with reference to FIG. 5.

Figure 8A:
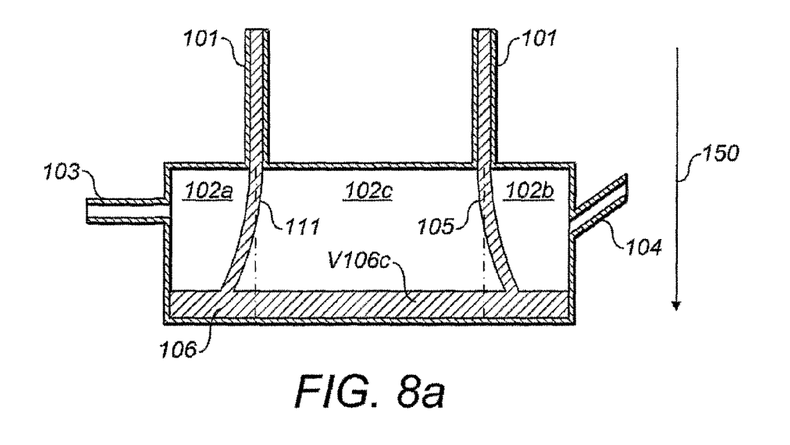
FIGS. 8a to 8c, illustrate configurations using two simultaneous liquid jets in an embodiment of the invention.

Some embodiments employ two or more liquid jets. FIG. 8a is a schematic illustration of the liquid jet deflection mechanism described above, using two liquid jets 105 and 111 flowing into a chamber 102, with a pressure increase in the volume defined in between the two liquid jets, resulting in two divergent deflections of the liquid jets 105 and 111. The jets 105 and 111 originate from the same or different upstream chambers containing the same liquid or different liquids. The pressure difference giving rise to the deflection of liquid jets 105 and 111 may result only from the pressure increase in the gas confined in the volume 102c, defined in between the two liquid jets 105 and 111. If, for example, the outlets 104 and 103 are set at constant atmospheric pressure, and chamber 102 is initially empty, the pressure difference responsible for the liquid jet deflection is governed by the relation:

$$\Delta p = p_i \frac{V_{102c}}{V_{102c} - V_{106c}}$$

where $V_{102c}$ is the volume of the compartment defined in between the two liquid jets and $V_{106c}$ is the volume of liquid accumulated in compartment 102c.

Figure 8B:
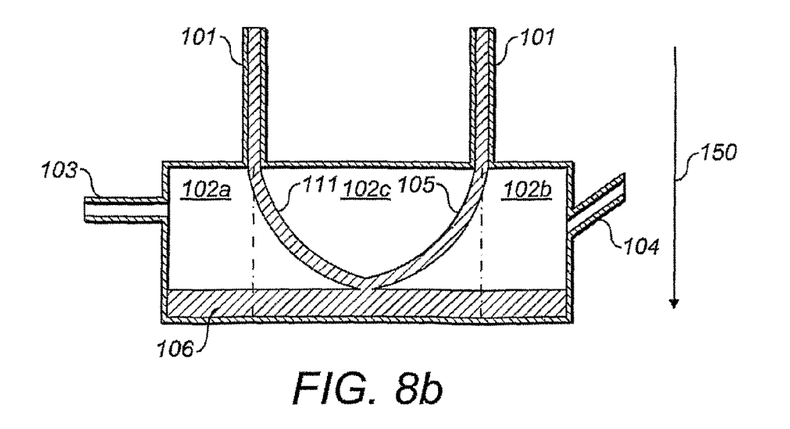

In some embodiments, two converging liquid jets are provided. FIG. 8b is a schematic illustration of the liquid jet deflection mechanism, using two liquid jets 105 and 111 flowing into a chamber 102. A pressure increase in the volumes defined outside the two liquid jets 102a and 102b results in two convergent deflections of the liquid jets 105 and 111. As the jets are forced towards each other these embodiments can, for example, improve liquid mixing. In this case, an additional inlet/outlet 122 (FIG. 9) may be placed in between the two liquid jets 105 and 111 in order to maintain a constant pressure in the volume 102c.

Figure 8C:
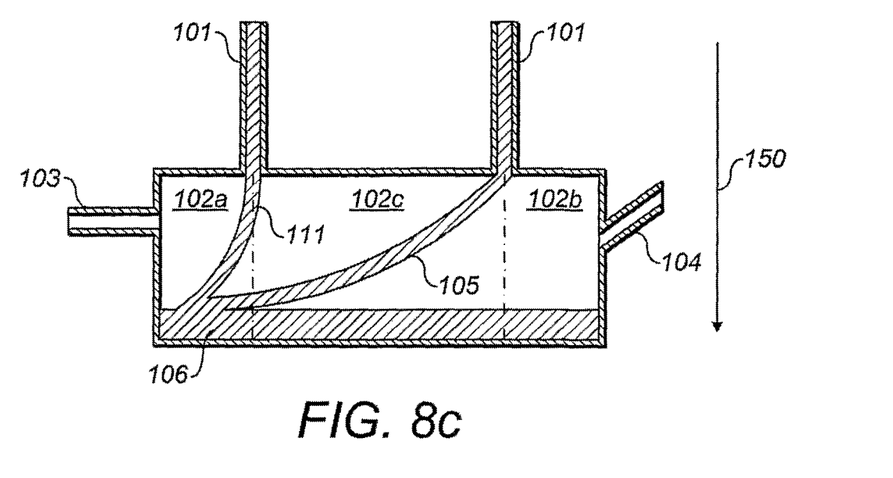

Some embodiment employing two liquid jets being deflected in the same direction are now described with reference to FIG. 8c. In this case the device is designed and operated to induce a pressure increase in one of the volumes defined outside the two liquid jets, resulting in deflections of the liquid jets in the same direction. This embodiment increases the contact surface (or contact time) at the junction of the two liquid jets, which may further enhance liquid mixing.

Some embodiments have three or more jets operating simultaneously. An example of the liquid jet deflection mechanism described above using three liquid jets 105, 111 and 123 flowing into a reservoir 102 is now described with reference to FIG. 9. The path of the central liquid jet 123 is shaped by controlling the flow rates of the other liquid jets 105 and 111, or adjusting the geometry and dimensions of the chamber 102 to have a direct impact on the pressure developed in the compartments 102a, 102b, 102c and 102d between the jets, or a combination of both effects. Flow rates of each individual jet can be adjusted using fluid propulsion mechanisms which are able to independently address each jet, or via design changes to the opening from which the jet is issued, or a combination of both. The system can also be used for adjusting the flow of the central liquid jet 123 with a constant deflection (or no deflection) by tuning the gas pressure in the vicinity of the central liquid jet 102c and 102d.

Figure 9:
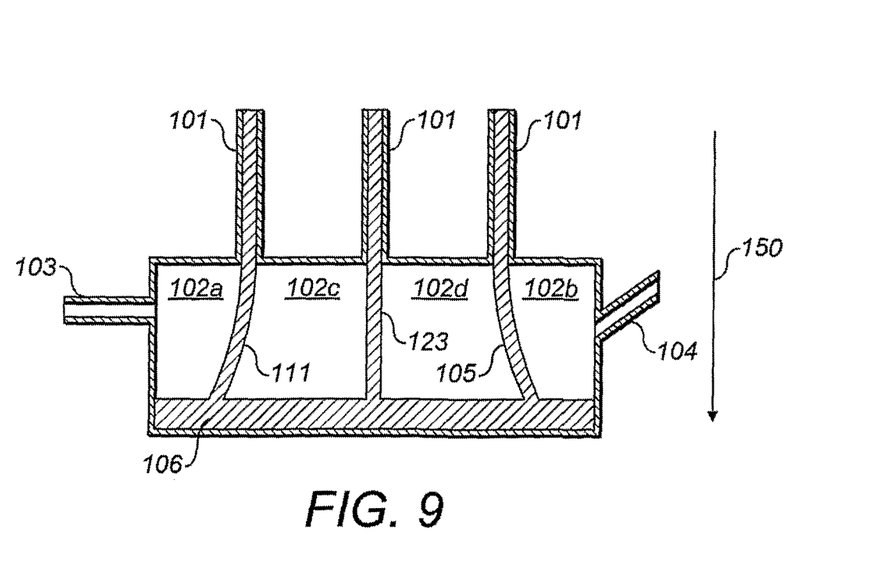
FIG. 9 illustrates a configuration using three simultaneous liquid jets in an embodiment of the invention.

Some embodiments of the three liquid jet system provide an ON/OFF valve for one of the liquid jets. In this particular case and above a certain gas pressure threshold, the flow of one liquid jet is stopped (OFF state) by acting on system parameters with influence the pressure developed in each compartment (e.g. jets flow rates and/or structure design). Once the gas pressure drops below the threshold the flow will resume (ON state). A simple embodiment of this ON/OFF valve consists of having the two lateral jets 105 and 111 with flow rates much higher than the central jet 123 and inducing a pressure increase in the space confined between them, which hinders the development of the central jet. In this case the central jet develops only after one or both lateral jets disappear as the upstream feeding chamber or chambers empty or their flow rate changes and the pressure in the space confined by them, drops below a threshold value. These embodiments find application in the sequential control of liquid flows.

While specific embodiments of the invention have been described above by way of example, many variations, modifications, alterations and combinations of the embodiments described above will be apparent to the skilled person.

In particular, although a specific design for centrifugal applications has only been described for the separation embodiment described with reference to FIG. 5, the remaining embodiments depicted schematically in what can be seen as a developed view can readily be adapted for centrifugal applications by the skilled person.

While FIG. 5g provides a particular example of the configuration and dimensions of the described embodiment by reference to the scale bar shown in the figure, it will be understood that the dimensions and configurations can readily be varied by the skilled person using simple principles to vary the parameters of the design. For example, the distance between the jet constraining surfaces can readily be varied as required and the formation of the two compartments on either side of the jet readily verified for each candidate design. Similarly, the distance and relative positioning of ports 164 and 162 can be varied as a function of whether plug formation is required or not, and on which time-scale and at which rotational speeds, the result being easily verified experimentally. It can thus be seen that the described embodiments can easily be varied in accordance with the specific applications, desired characteristics being readily verifiable by simple experiments, trying out the altered designs.

For example, in some applications the deflection mechanism described above is combined with additional control using external elements, in a passive or active mode. Pressure control may be obtained, for example, by using an external flow control mechanism acting directly on the liquid arriving in chamber 102, or by using an additional gas pressure control over chamber 102 or some of the compartments defined by the liquid jets and/or the reservoir 109. External control mechanisms can be activated for example when the liquid jet 105 or accumulating liquid volume 106 arrive at a specific location in the chamber 102, or when the liquid jet 105 presents a specific shape. This implementation may use additional external elements, such as flow detectors, contact detectors or light detectors. The control may be adjusted in order to obtain predefined liquid jet deflections that are considered suitable for particular applications.

It will be understood that in embodiments where one or more of the ports described is permanently maintained closed, the ports may be omitted from the design as redundant.

The present invention may be used in a wide range of applications involving liquid flow, in particular but not limited to chemical and biological detection systems. Other implementations exploiting the liquid jet deflection mechanism described above are equally envisaged in macroscopic or microscopic fluidic systems, using external or internal additional pressure control elements.

The present invention is thus not intended to be limited to the particular described embodiments and examples but is defined by the appendent claims.

The invention claimed is:

1. A fluid flow control system comprising:
a fluid flow control chamber,
means for injecting a liquid into the fluid flow control chamber to form a liquid membrane dividing the chamber into compartments on each side of the liquid membrane, and
means for generating a pressure differential between the compartments to control a deflection of the injected liquid.

2. A system as claimed in claim 1, in which the means for injecting the liquid include means for creating a centrifugal force acting on the liquid.

3. A system as claimed in claim 1, in which the means for generating the pressure differential include the means for injecting the liquid.

4. A system as claimed in claim 1, wherein the means for injecting the liquid includes a liquid reservoir connected to the fluid flow control chamber by a liquid passage enabling injection of liquid from the reservoir into the fluid flow control chamber and by a vent passage for venting the control chamber into the reservoir.

5. A system as claimed in claim 4, including means for stopping flow of liquid from the liquid reservoir to the fluid flow control chamber by deflecting the injected liquid into the vent passage to form a liquid plug in the vent passage.

6. A system as claimed in claim 5, in which the means for stopping flow include means for creating a pressure decrease in the vent passage as liquid flows from the liquid reservoir to the fluid flow chamber.

7. A system as claimed in claim 5, including means for re-starting the flow of liquid by changing a force acting on the liquid plug.

8. A system as claimed in claim 4, including means for trapping a heavier component or components of the liquid in the liquid reservoir and injecting a lighter component or components into the fluid flow control chamber.

9. A system as claimed in claim 8, including means for trapping a heavier component or components of the liquid in the fluid flow control chamber.

10. A system as claimed in claim 1, including means for aliquoting the liquid as it is injected into the fluid flow control chamber.

11. A system as claimed in claim 1, including means for injecting a liquid to form a plurality of liquid membranes in the fluid flow control chamber.

12. A system as claimed in claim 1, in which the fluid flow chamber is defined between two surfaces for containing the membrane, the surfaces being less than 1 mm apart.

13. A system as claimed in claim 1, in which the fluid flow chamber is defined between two surfaces for containing the membrane, the surfaces being less than 0.5 mm apart.

14. A device for containing a fluid, the device defining a first volume containing a gas and a first port through which a liquid can be injected into the first volume to partition the first volume into separate compartments on each side of the liquid; the device being configured to convert flow of the liquid into the first volume into a pressure differential between the compartments, thereby deflecting the liquid.

15. A device as claimed in claim 14, defining a second volume in fluidic communication with the first port and further fluidically connected to the first volume by a vent passage to one side of the first port such that the gas can vent to the second volume as liquid is injected into the first volume.

16. A device as claimed in claim 15, in which the device is configured to create a pressure decrease in the vent passage when a liquid level in the second volume decreases.

17. A device as claimed in claim 15, the device defining an axis of rotation about which the device is rotatable to centrifugally drive the injection of liquid, the first volume being located radially outward of the second volume and the vent passage connects to the first volume radially outward of the first port.

18. A device as claimed in claim 17, in which an end of the vent passage connecting to the first volume is the radially outmost portion of the vent passage.

19. A device as claimed in claim 17, in which the second volume comprises a portion radially between a second port connecting the second volume to the first port and the first volume.

20. A device as claimed in claim 19, in which the first volume is in fluid communication with a third volume through a third port, wherein a portion of the first volume is located radially beyond the third port.

21. A device as claimed in claim 20, in which the third volume defines a metering device.

22. A device as claimed in claim 15, in which the second volume comprises two chambers connected by a passage.

23. A device as claimed in claim 14, the device defining an axis of rotation about which the device is rotatable to centrifugally drive the injection of liquid.

24. A device as claimed in claim 14, defining a plurality of metering structures opposite the first port to one side of it such that successive metering structures are filled by the liquid jet as the jet is deflected.

25. A device as claimed in claim 14, in which the device is configured to centrifugally separate components of a sample, the sample having a volume in the range of 1 to 20 microlitres.

26. A device as claimed in claim 25, wherein the sample is a blood sample and the centrifugally separated components include plasma.

27. A device as claimed in claim 14, in which the first volume is defined between surfaces for containing the liquid separating the compartments, the surfaces being less than 1 mm apart.

28. A system as claimed in claim 14, in which the fluid flow chamber is defined between two surfaces for containing the membrane, the surfaces being less than 0.5 mm apart.

29. A method of controlling fluid flow in a chamber, including injecting a liquid into the chamber to divide the chamber into compartments on each side of the injected liquid and generating a pressure differential between the compartments to control a deflection of the injected liquid.

30. A method as claimed in claimed in claim 29, including creating the pressure differential by injecting the liquid into the chamber.

31. A method as claimed in claimed in claim 29, including injecting the liquid into the chamber by injecting the liquid from a reservoir connected to the chamber, equilibrating pressures between the chamber and the reservoir by a vent passage connecting the chamber to the reservoir, and stopping the injection of liquid by deflecting the injected liquid into the vent passage to form a liquid plug.

32. A method as claimed in claim 31, including applying a first centrifugal force to the reservoir and chamber to form the liquid plug, then applying a second centrifugal force, to centrifugally separate components of the liquid and then applying a third centrifugal force, different from the first and second centrifugal forces, to dislodge the liquid plug and transfer a fraction of the liquid in the reservoir to the chamber.

33. A method as claimed in claim 32, including wherein the second centrifugal force is the same as the first centrifugal force.

34. A method as claimed in claim 31, including creating a negative pressure in the vent passage by injecting the liquid from the reservoir into the chamber.

35. A method as claimed in claim 29, including using a centrifugal force to inject the liquid.

* * * * *